(12) United States Patent
Law et al.

(10) Patent No.: US 6,905,804 B2
(45) Date of Patent: *Jun. 14, 2005

(54) ELECTROPHOTOGRAPHIC ORGANOPHOTORECEPTORS WITH NOVEL CHARGE TRANSPORT MATERIALS

(75) Inventors: Kam W. Law, Woodbury, MN (US); Nusrallah Jubran, St. Paul, MN (US); Zbigniew Tokarski, Woodbury, MN (US); Alan R. Katritzky, Gainesville, FL (US); Ritu Jain, Gainesville, FL (US); Rexiat Maimait, Cincinnati, OH (US)

(73) Assignee: Samsung Electronics Co., Ltd., Suwon (KR)

(*) Notice: Subject to any disclaimer, the term of this patent is extended or adjusted under 35 U.S.C. 154(b) by 31 days.

This patent is subject to a terminal disclaimer.

(21) Appl. No.: 10/349,811

(22) Filed: Jan. 22, 2003

(65) Prior Publication Data

US 2003/0198880 A1 Oct. 23, 2003

Related U.S. Application Data

(60) Provisional application No. 60/355,018, filed on Feb. 8, 2002, provisional application No. 60/355,047, filed on Feb. 8, 2002, provisional application No. 60/355,060, filed on Feb. 8, 2002, provisional application No. 60/355,228, filed on Feb. 8, 2002, provisional application No. 60/355,080, filed on Feb. 8, 2002, provisional application No. 60/355,079, filed on Feb. 8, 2002, provisional application No. 60/355,073, filed on Feb. 8, 2002, provisional application No. 60/355,066, filed on Feb. 8, 2002, and provisional application No. 60/355,019, filed on Feb. 8, 2002.

(51) Int. Cl.$^7$ .............................................. G03G 5/047
(52) U.S. Cl. ................ 430/58.45; 430/58.4; 430/58.5; 430/58.55
(58) Field of Search ..................... 430/58.45, 58.4, 430/58.5, 58.55, 72, 75, 76, 77

(56) References Cited

U.S. PATENT DOCUMENTS

| | | | |
|---|---|---|---|
| 4,297,426 A | 10/1981 | Sakai et al. | 430/59 |
| 4,415,640 A | * 11/1983 | Goto et al. | 430/58.4 |
| 4,476,137 A | 10/1984 | Haviv et al. | 424/272 |
| 4,786,571 A | 11/1988 | Ueda | 430/59 |
| 4,957,838 A | 9/1990 | Aruga et al. | 430/59 |
| 5,128,227 A | 7/1992 | Monbaliu et al. | 430/59 |
| 5,274,116 A | 12/1993 | Martin et al. | 548/465 |
| 5,932,384 A | 8/1999 | Mitsumori et al. | 430/59 |
| 6,001,522 A | 12/1999 | Woo et al. | 430/65 |
| 6,004,708 A | 12/1999 | Bellino et al. | 430/58.45 |
| 6,020,096 A | 2/2000 | Fuller et al. | 430/58.35 |
| 6,030,734 A | 2/2000 | Mitsumori | 430/58.8 |
| 6,066,426 A | 5/2000 | Mott et al. | 430/58.2 |
| 6,099,996 A | 8/2000 | Yanus et al. | 430/58.8 |
| 6,140,004 A | 10/2000 | Mott et al. | 430/132 |
| 6,214,503 B1 | 4/2001 | Gaidelis et al. | 430/58.45 |
| 6,340,548 B1 | 1/2002 | Jubran et al. | 430/58.45 |
| 6,350,553 B2 * | 2/2002 | Srinivasan | 430/135 |
| 6,689,523 B2 * | 2/2004 | Law et al. | 430/58.35 |

FOREIGN PATENT DOCUMENTS

| | | | |
|---|---|---|---|
| GB | 1047525 | 11/1966 | C07D/63/02 |
| JP | XP-002240965 | 9/1990 | G03G/5/05 |
| JP | XP-002240966 | 9/1990 | C07C/251/84 |
| JP | XP-002240967 | 9/1990 | C03G/5/06 |

OTHER PUBLICATIONS

Atherton, F. R., et al., "Synthesis of 3(s)–Acylamino–1–[(Phenyl) (1H–Tetrazol–5–YL) Amino]–2–Azetidinones," *Tetrahedron* vol. 39, No. 15, pp. 2599–2608, 1983.

Boyd, G. V., "The Dimerisation of 5–Methylene—Δ2–1,3, 4–Oxadiazolines," *Journal of The Chemical Society* (C), pp. 2314–2317, 1971.

Murakami, Y., et al. "An Efficient Synthesis of 1, 1–Disubtituted Hydrazines," *Chemical and Pharmaceutical Bulletin* vol. 31, No. 2, pp. 423–428, 1983.

* cited by examiner

*Primary Examiner*—John L. Goodrow
(74) *Attorney, Agent, or Firm*—Patterson, Thuente, Skaar & Christensen, P.A.

(57) ABSTRACT

This invention relates to a novel organophotoreceptor that includes:

(a) a charge transport material comprising a fluorenone hydrazone having a) at least two fluorenone alkylsulfonylphenylhydrazone groups, b) at least two fluorenone pyrrolylhydrazone groups, c) at least two fluorenone benzotriazolylhydrazone groups, d) at least two fluorenone sulfolanylhydrazone groups, e) at least two fluorenone pyrazolylhydrazone groups, f) at least two fluorenone naphthylhydrazone groups, g) at least two fluorenone tetrazolylhydrazone groups, h) at least two fluorenone stilbenylhydrazone groups, or i) at least two fluorenone (9H-fluoren-9-ylidene)benzylhydrazone groups. Some of these fluoreneones may be represented by the formula

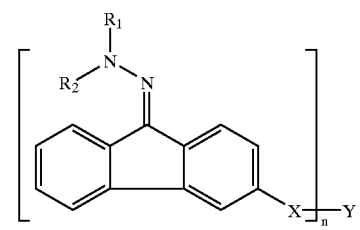

where n is an integer between 2 and 6, inclusive; $R_1$ is hydrogen, an alkyl group, or an aryl group; $R_2$ is an alkylsulfonylphenyl or one of its derivatives; X is a linking group. The compounds may form electrostatic imaging systems in combination with (b) a charge generating compound; and
(c) an electrically conductive substrate.

10 Claims, No Drawings

ELECTROPHOTOGRAPHIC ORGANOPHOTORECEPTORS WITH NOVEL CHARGE TRANSPORT MATERIALS

CROSS REFERENCE TO RELATED APPLICATIONS

This application claims priority to copending U.S. Provisional Patent Application Ser. Nos. 60/355,018, 60/355,047, 60/355,060, 60/355,228, 60/355,080, 60/355,079, 60/355,073, 60/355,066, and 60/355,019, all of which are filed on Feb. 8, 2002.

BACKGROUND OF THE INVENTION

1. Field of the Invention

This invention relates to organophotoreceptor suitable for use in electrophotography and, more specifically, to flexible organophotoreceptor having novel charge transport materials. The generic class of charge transport materials are fluorenone hydrazones having a) at least two fluorenone alkylsulfonylphenylhydrazone groups, b) at least two fluorenone pyrrolylhydrazone groups, c) at least two fluorenone benzotriazolylhydrazone groups, d) at least two fluorenone sulfolanylhydrazone groups, e) at least two fluorenone pyrazolylhydrazone groups, f) at least two fluorenone naphthylhydrazone groups, g) at least two fluorenone tetrazolylhydrazone groups, h) at least two fluorenone stilbenylhydrazone groups, and i) at least two fluorenone (9H-fluoren-9-ylidene)benzylhydrazone groups.

2. Background of the Art

In electrophotography, an organophotoreceptor in the form of a plate, a flexible belt, a disk, a rigid drum, or a sheet around a rigid or compliant drum having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas, thereby forming a pattern of charged and uncharged areas (referred to as latent image). A liquid or solid toner is then provided in the vicinity of the latent image, and the toner particles deposit in either the charged or uncharged areas to create a toned image on the surface of the photoconductive layer. The resulting visible toner image can be transferred to a suitable receiving surface such as paper, or the photoconductive layer can operate as a permanent receptor for the image. The imaging process can be repeated many times.

Both single layer and multilayer photoconductive elements have been used. In the single layer embodiment, a charge transport material and charge generating material are combined with a polymeric binder and then deposited on an electrically conductive substrate. In the multilayer embodiment, the charge transport material and charge generating material are in the form of separate layers, each of which can optionally be combined with a polymeric binder and deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single layer and multilayer photoconductive elements, the purpose of the charge generating material is to generate charge carriers (i.e., holes or electrons) upon exposure to light. The purpose of the charge transport material is to accept these charge carriers and transport them through the charge transport layer in order to discharge a surface charge on the photoconductive element. The charge transport material can be a charge transport compound, an electron transport compound, or a combination of both. When a charge transport compound is used, the charge transport compound accepts the hole carriers and transports them through the layer containing the charge transport compound. When an electron transport compound is used, the electron transport compound accepts the electron carriers and transports them through the layer containing the electron transport compound.

To produce high quality images, it is desirable to maximize the amount of charge which the charge transport material, such as electron transport compound, can accept (indicated by a parameter known as the acceptance voltage or "$V_{acc}$"), and to minimize retention of that charge upon discharge (indicated by a parameter known as the discharge voltage or "$V_{dis}$").

There are many charge transport materials available for electrophotography. The most common charge transport materials are pyrazoline derivatives, fluorene derivatives, oxadiazole derivatives, stilbene derivatives, hydrazone derivatives, carbazole hydrazone derivatives, triphenylamine derivatives, julolidine hydrazone derivatives, polyvinyl carbazole, polyvinyl pyrene, or polyacenaphthylene. However, each of the above charge transport materials suffers some disadvantages. There is always a need for novel charge transport materials to meet the various requirements of electrophotography applications.

SUMMARY OF THE INVENTION

In a first aspect, the invention features an organophotoreceptor that includes:

a) a charge transport material comprising a fluorenone hydrazone, the fluorenone hydrazone having a) at least two fluorenone alkylsulfonylphenylhydrazone groups, b) at least two fluorenone pyrrolylhydrazone groups, c) at least two fluorenone benzotriazolylhydrazone groups, d) at least two fluorenone sulfolanylhydrazone groups, e) at least two fluorenone pyrazolylhydrazone groups, f) at least two fluorenone naphthylhydrazone groups, g) at least two fluorenone tetrazolylhydrazone groups, h) at least two fluorenone stilbenylhydrazone groups, or i) at least two fluorenone (9H-fluoren-9-ylidene)benzylhydrazone groups;

(b) a charge generating compound; and (c) an electrically conductive substrate.

The charge transport material may be represented by the following formula

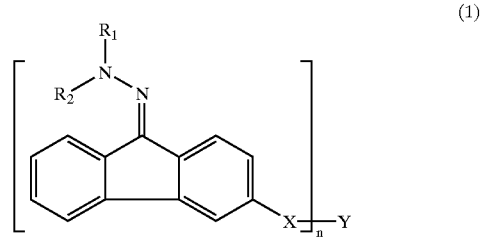

(1)

where n is an integer between 2 and 6, inclusive;

$R_1$ is hydrogen, an alkyl group, or an aryl group (e.g., phenyl, naphthyl, stilbenyl, benzyl, or tolanyl group, see U.S. Pat. No. 6,469,123 for a complete description and structure of this group);

$R_2$ is an alkylsulfonylphenyl group, a pyrrolyl group, a benzotriazolyl group, a sulfolanyl group, a pyrazolyl group, a naphthyl group, a tetrazolyl group, a stilbenyl group, a (9H-fluoren-9-ylidene)benzyl group, or one of their derivatives having substituents thereon that do not alter the underlying elemental content or bond structure (e.g., changing double bonds to single bonds and single bonds to double bonds) of the recited group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group (e.g., a cyclotetrasiloxyl group), a heterocyclic group, or a $CR_7$ group where $R_7$ is hydrogen atom, an alkyl group, or an aryl group.

The charge transport material may or may not be symmetrical. Thus, for example, a linking group X for any given "arm" of the compound may be the same or different from the linking groups in other "arms" of the compound. Similarly, $R_1$ and $R_2$ groups for any given "arm" of the compound may be the same or different from $R_1$ and $R_2$ groups in any other arm. In addition, the above-described formula for the charge transport material is intended to cover isomers. The organophotoreceptor may be provided in the form of a plate, a flexible belt, a disk, a rigid drum, or a sheet around a rigid or compliant drum. In one embodiment, the organophotoreceptor includes: (a) a charge transport layer comprising the charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate.

In various aspects, the invention features an electrophotographic imaging apparatus that includes (a) a plurality of support rollers; and (b) the above-described organophotoreceptor in the form of a flexible belt threaded around the support rollers. The apparatus preferably further includes a liquid toner dispenser. In another aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) contacting the surface with a liquid toner that includes a dispersion of colorant particles in an organic liquid to create a toned image; and (d) transferring the toned image to a substrate. In still another aspect, the invention features a novel charge transport material having Formula 1 above These organophotoreceptor can be used successfully with liquid toners to produce high quality images. The high quality of the images can be maintained after repeated cycling. Other features and advantages of the invention will be apparent from the following description of the preferred embodiments thereof, and from the claims.

DETAILED DESCRIPTION OF THE INVENTION

The invention features organophotoreceptor that include charge transport materials having the formula set forth in the Summary of the Invention above. In addition, various subgeneric formulae may represent compounds of a more limited scope that are useful in the practice of the present invention. In addition to the scope of:

a) a charge transport material comprising a fluorenone hydrazone, the fluorenone hydrazone having a) at least two fluorenone alkylsulfonylphenylhydrazone groups, b) at least two fluorenone pyrrolylhydrazone groups, c) at least two fluorenone benzotriazolylhydrazone groups, d) at least two fluorenone sulfolanylhydrazone groups, e) at least two fluorenone pyrazolylhydrazone groups, f) at least two fluorenone naphthylhydrazone groups, g) at least two fluorenone tetrazolylhydrazone groups, h) at least two fluorenone stilbenylhydrazone groups, or i) at least two fluorenone (9H-fluoren-9-ylidene)benzylhydrazone groups;

(b) a charge generating compound; and (c) an electrically conductive substrate.

The charge transport material may be represented by the following formula

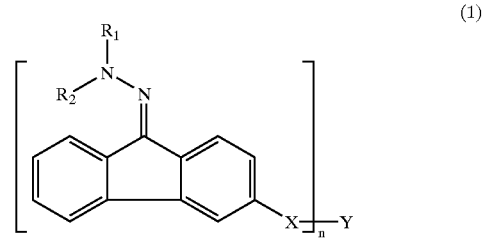

(1)

where n is an integer between 2 and 6, inclusive;

$R_1$ is hydrogen, an alkyl group, or an aryl group (e.g., phenyl, naphthyl, stilbenyl, benzyl, or tolanyl group, see U.S. Pat. Nos. 6,469,123; 6,423,811; and 6,313,185 and for a complete description and structure of this group, which patents are incorporated herein by reference for the disclosure of that group); $R_2$ is an alkylsulfonylphenyl group, a pyrrolyl group, a benzotriazolyl group, a sulfolanyl group, a pyrazolyl group, a naphthyl group, a tetrazolyl group, a stilbenyl group, a (9H-fluoren-9-ylidene)benzyl group, or one of their derivatives;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group (e.g., a cyclotetrasiloxyl group), a heterocyclic group, or a $CR_7$ group where $R_7$ is hydrogen atom, an alkyl group, or an aryl group.

Narrower descriptions of subgroups of compounds within the generic scope of the invention include, by way of non-limiting examples,

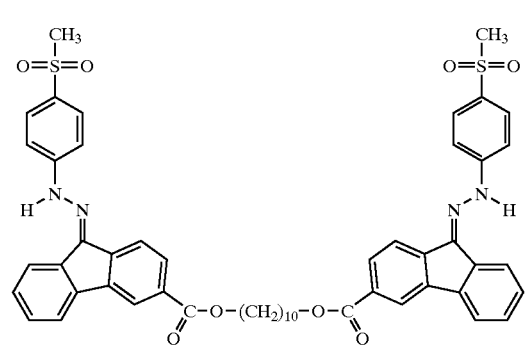
(2)
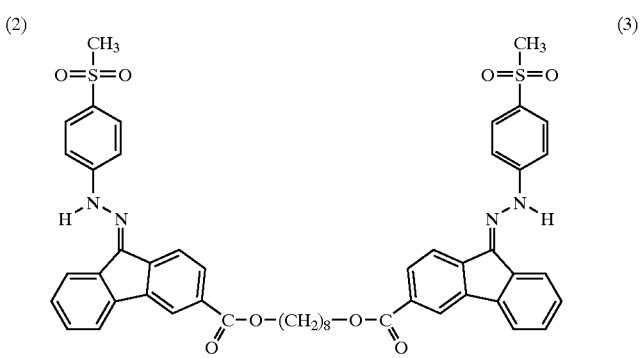
(3)
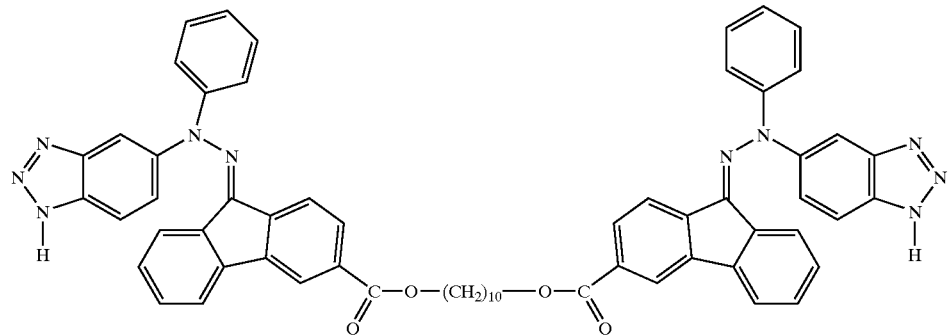
(4)
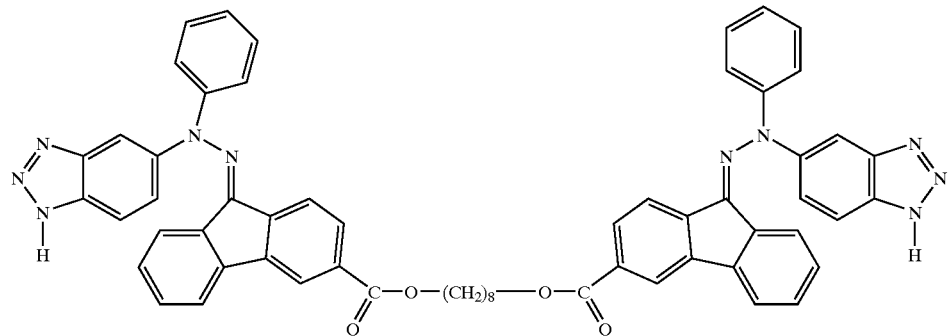
(5)
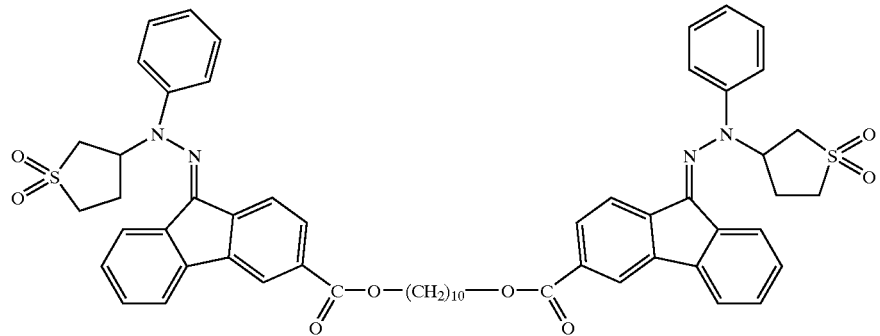
(6)

-continued
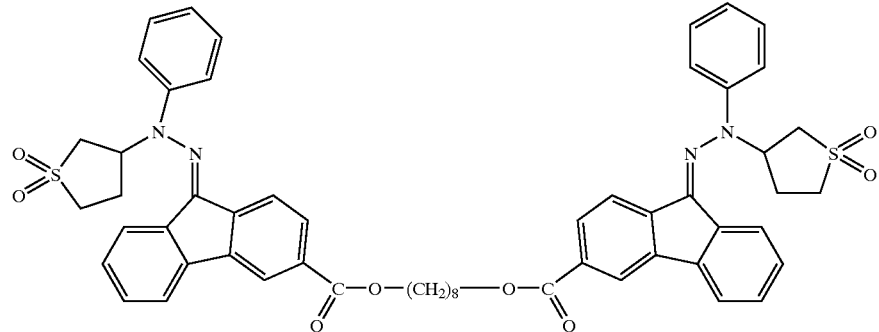
(7)
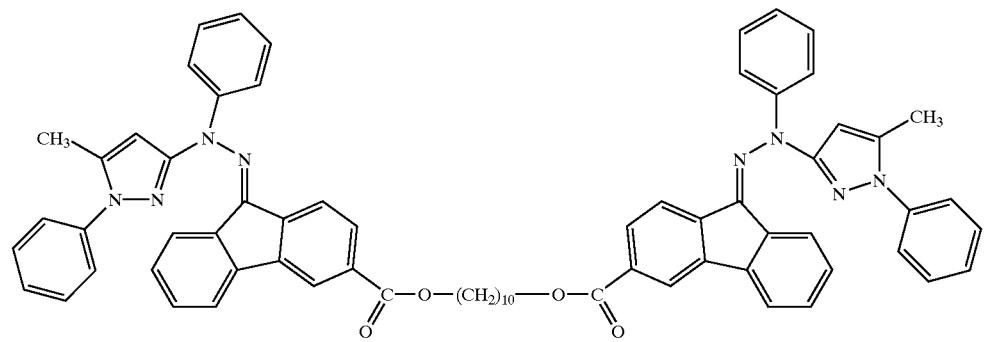
(8)
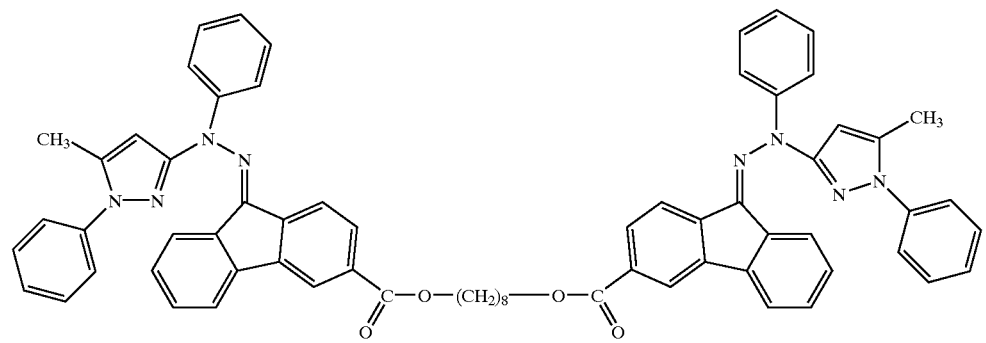
(9)
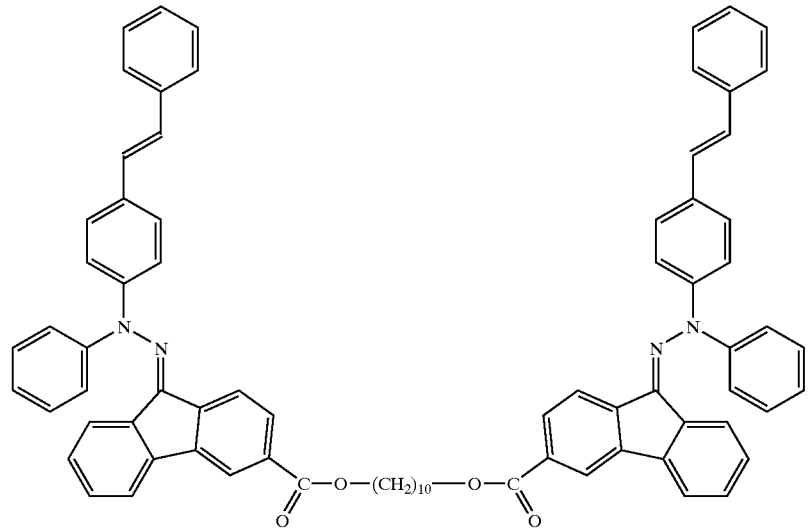
(10)

-continued
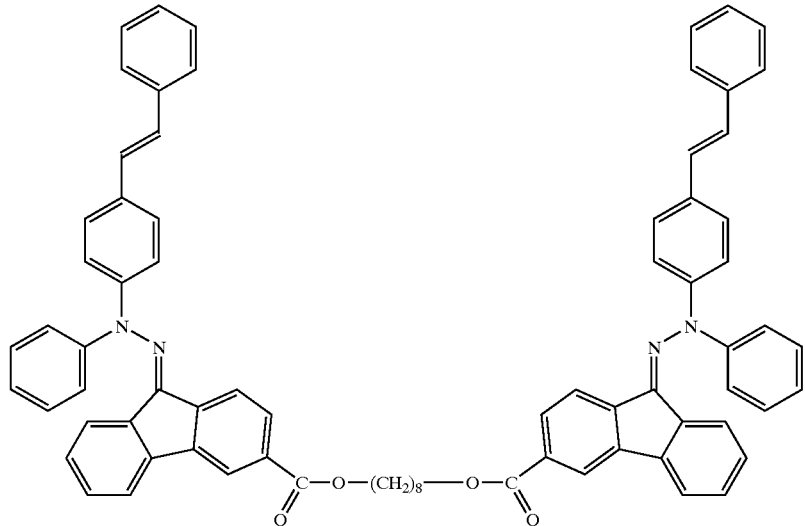
(11)
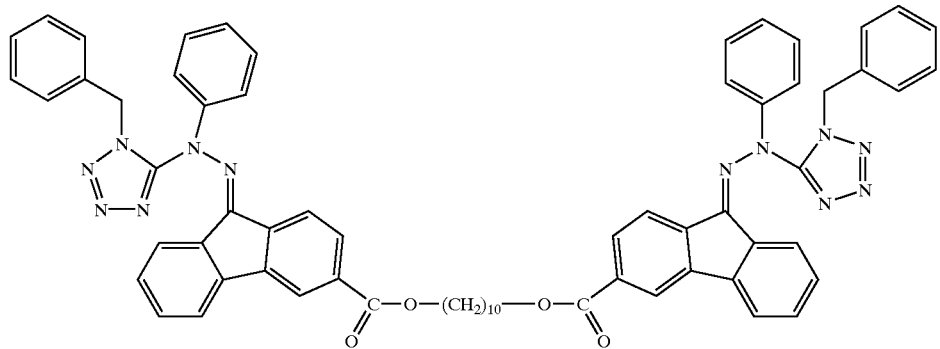
(12)
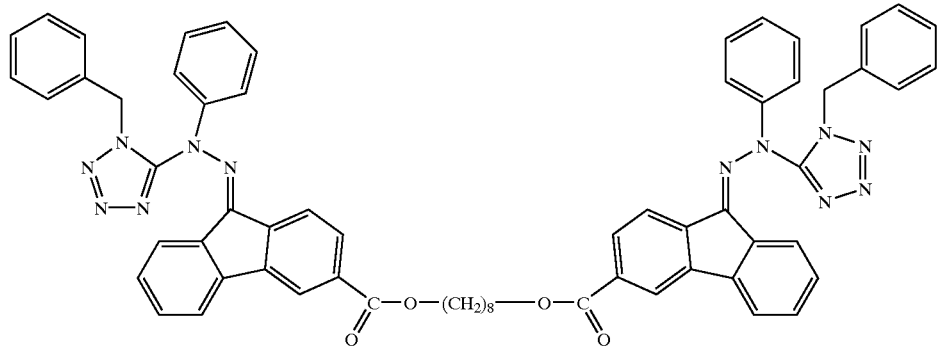
(13)
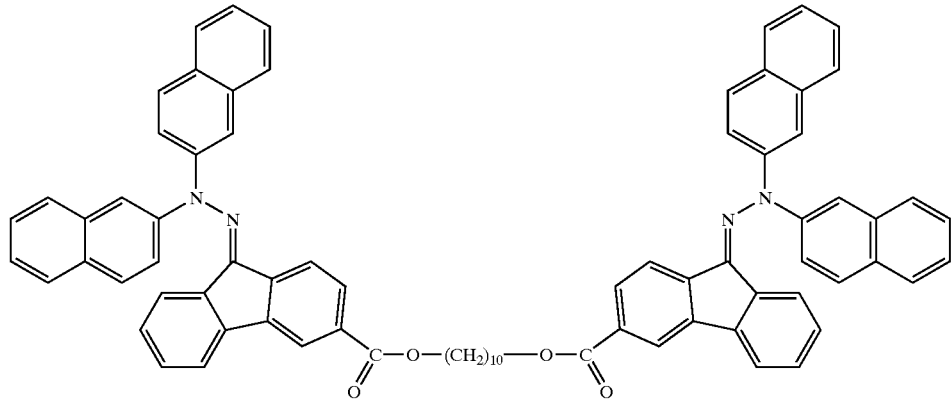
(14)

-continued
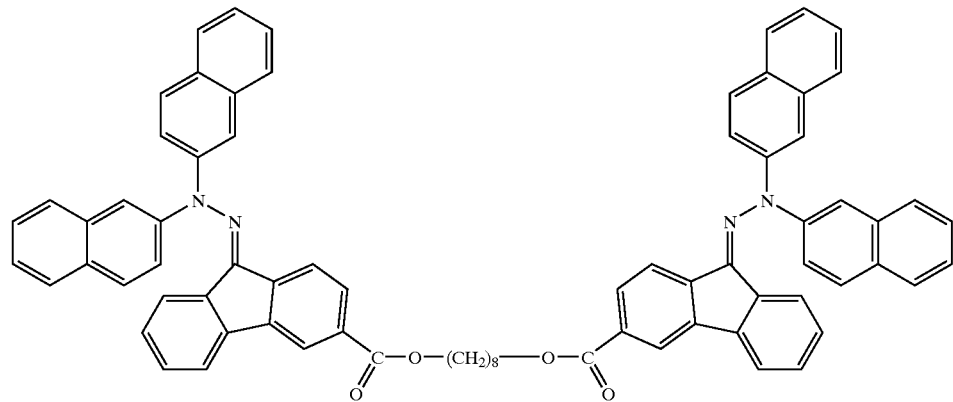
(15)
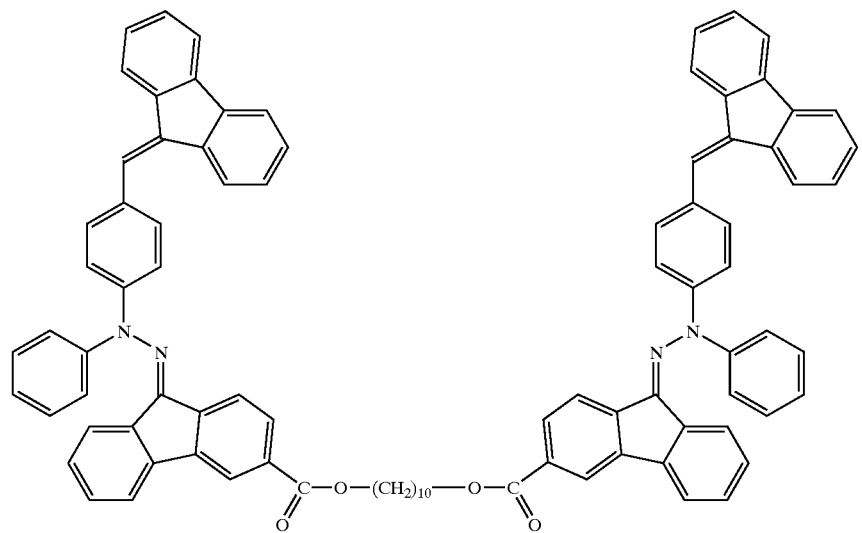
(16)
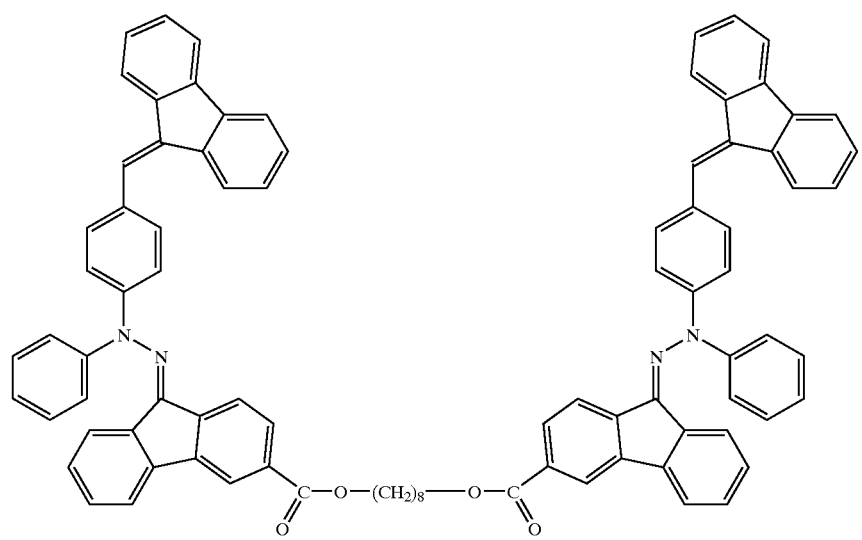
(17)

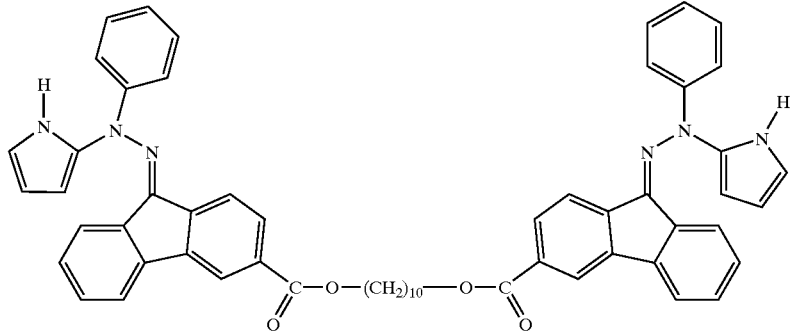

(18)

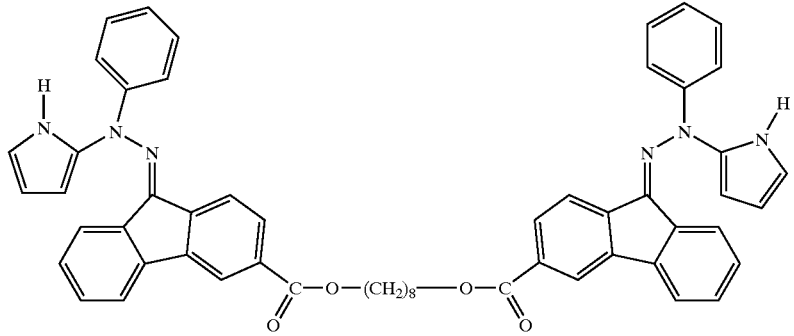

(19)

The electrically conductive substrate may be flexible, for example in the form of a flexible web or a belt, or inflexible, for example in the form of a drum. Typically, a flexible electrically conductive substrate comprises of an insulated substrate and a thin layer of electrically conductive materials. The insulated substrate may be paper or a film forming polymer such as polyethylene terephthalate, polyimide, polysulfone, polyethylene naphthalate, polypropylene, nylon, polyester, polycarbonate, polyvinyl fluoride, polystyrene and the like. Specific examples of supporting substrates included polyethersulfone (Stabar S-100, available from ICI), polyvinyl fluoride (Tedlar™, available from E.I. DuPont de Nemours & Company), polybisphenol-A polycarbonate (Makrofol®, available from Mobay Chemical Company) and amorphous polyethylene terephthalate (Melinar®, available from ICI Americas, Inc.). The electrically conductive materials may be graphite, dispersed carbon black, iodide, conductive polymers such as polypyroles and Calgon Conductive Polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. Preferably, the electrically conductive material is aluminum. Typically, the photoconductor substrate will have a thickness adequate to provide the required mechanical stability. For example, flexible web substrates generally have a thickness from about 0.01 to about 1 mm, while drum substrates generally have a thickness of from about 0.5 mm to about 2 mm.

The charge generating compound is a material which is capable of absorbing light to generate charge carriers, such as a dyestuff or pigment. Examples of suitable charge generating compounds include metal-free phthalocyanines, metal phthalocyanines such as titanium phthalocyanine, copper phthalocyanine, oxytitanium phthalocyanine, hydroxygallium phthalocyanine, squarylium dyes and pigments, hydroxy-substituted squarylium pigments, perylimides, polynuclear quinones available from Allied Chemical Corporation under the tradename INDOFAST™ Double Scarlet, INDOFAST™ Violet Lake B, IDOFAST™ Brilliant Scarlet and INDOFAST™ Orange, quinacridones available from DuPont under the tradename MONASTRAL™ Red, MONASTRAL™™ Violet and MONASTRAL™™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulfoselenide, cadmiumselenide, cadmium sulfide, and mixtures thereof. Preferably, the charge generating compound is oxytitanium phthalocyanine, hydroxygallium phthalocyanine or a combination thereof.

Preferably, the charge generation layer comprises a binder in an amount of from about 10 to about 90 weight percent and more preferably in an amount of from about 20 to about 75 weight percent, based on the weight of the charge generation layer.

The binder is capable of dispersing or dissolving the charge transport material (in the case of the charge transport layer) and the charge generating compound (in the case of the charge generating layer). Examples of suitable binders for both the charge generating layer and charge transport layer include polystyrene-co-butadiene, modified acrylic polymers, polyvinyl acetate, styrene-alkyd resins, soya-alkyd resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak resins, resol resins, poly(phenylglycidyl ether)-co-dicyclopentadiene, copolymers of monomers used for the above-mentioned polymers, and combinations thereof. Polycarbonate binders and polyvinyl butyral are particularly preferred. Example of suitable polycarbonate binders include polycaronate A which is derived from bisphenol-A, polycarbonate Z, which is derived from cyclohexylidene bisphenol, polycarbonate C, which is derived from methyl-bisphenol A, and polyestercarbonates. Examples of suitable polyvinyl butyral are BX-1 and BX-5 form Sekisui Chemical Co. Ltd., Japan.

Optionally, the organophotoreceptor may include a second charge transport material as known in the art. The charge transport material can be a charge transport compound, an electron transport compound, or a combination of both. When a charge transport compound is used, the charge transport compound accepts the hole carriers and transports them through the layer containing the charge transport compound. When an electron transport compound is used, the electron transport compound accepts the electron carriers and transports them through the layer containing the electron transport compound.

Suitable charge transport compounds include, but are not limited to, pyrazoline derivatives, fluorene derivatives, oxadiazole derivatives, stilbene derivatives, hydrazone derivatives, carbazole hydrazone derivatives, triaryl amines, polyvinylcarbazole, polyvinylpyrene, polyacenaphthylene, or multi-hydrazone compounds comprising at least two hydrazone groups and at least two groups selected from the group consisting of triphenylamine and heterocycles such as carbazole, julolidine, phenothiazine, phenazine, phenoxazine, phenoxathiin, thiazole, oxazole, isoxazole, dibenzo(1,4)dioxine, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Non-limiting examples of suitable electron transport compound include bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-one, and 1,3,7-trinitrodibenzothiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethyl-idene)thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)-malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxycarbonyl)methylene]anthrone, 1,8-dihydroxy-10-[bis(ethoxycarbonyl)methylene]anthrone, and 1-cyano-10-[bis(ethoxycarbonyl)methylene]anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitrothioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyanoquinoedimethane, 2,4,5,7-tetranitro-9-fluorenone, 5 2,4,7-trinitro-9-dicyanomethylenefluorenone, 2,4,5,7-tetranitroxanthone derivatives, and 2,4,8-trinitrothioxanthone derivatives.

Optionally, the photoconductive layer of this invention may contain a light stabilizer. Non-limiting examples of suitable light stablizer include hindered trialkylamines such as TINUVIN® 292 (from Ciba Specialty Chemicals, Terrytown, N.Y.), hindered alkoxydialkylamines such as TINUVIN® 123 (from Ciba Specialty Chemicals), benzotriazoles such as TINUVIN® 928 (from Ciba Specialty Chemicals), benzophenones, nickel compounds such as ARBESTAB™ (from Robinson Brothers Ltd, West Midlands, Great Britain), salicylates, cyanocinnamates, benzylidene malonates, benzoates, oxanilides, polymeric sterically hindered amines such as LUCHEM™ (from atochem North America, Buffalo, N.Y.). Preferably, the light stabilizer is selected from the group consisting of hindered trialkylamines having the following formula:

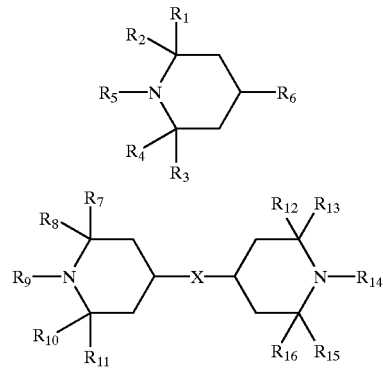

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independently, hydrogen, alkyl group, or ester, or ether group; and $R_5$, $R_9$, and $R_{14}$ are, independently, alkyl group; and X is a linking group selected from the group consisting of —O—CO—(CH$_2$)$_m$—CO—O— where m is between 2 to 20.

The light stabilizer in the photoconductive layer is in an amount of from about 0.5 to about 25 weight percent and more preferably in an amount of from about 1 to about 10 weight percent, based on the weight of the photoconductive layer.

Conveniently, the photoconductive layer may be formed by dispersing or dissolving the components such as a charge generating compound, a charge transport compound, a light stabilizer, an electron transport compound, and a polymeric binder in organic solvent, coating the dispersion and/or solution on the respective underlying layer and drying the coating. Preferably, the components are dispersed by high shear homogenization, ball-milling, attritor milling, high energy bead (sand) milling or other size reduction processes or mixing means known in the art for effecting particle size reduction in forming a dispersion.

The organophotoreceptor may include additional layers as well. Such layers are well-known and include, for example, barrier layers, release layers, adhesive layer, and sub-layer. The release layer forms the uppermost layer of the photoconductor element with the barrier layer sandwiched between the release layer and the photoconductive element. The adhesive layer locates and improves the adhesion between the barrier layer and the release layer. The sub-layer is a charge blocking layer and locates between the electrically conductive substrate and the photoconductive element. The sub-layer may also improve the adhesion between the electrically conductive substrate and the photoconductive element.

Suitable barrier layers include coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyninyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above organic binders optionally may contain small inorganic particles such as fumed silica, silica, titania, alumina, zirconia, or a combination thereof. The typical particle size is in the range of 0.001 to 0.5 micrometers, preferably 0.005 micrometers. A preferred barrier layer is a 1:1 mixture of methyl cellulose and methyl vinyl ether/maleic anhydride copolymer with glyoxal as a crosslinker.

The release layer topcoat may comprise any release layer composition known in the art. Preferably, the release layer is a fluorinated polymer, siloxane polymer, fluorosilicone polymer, silane, polyethylene, polypropylene, polyacrylate, or a combination thereof. More preferably, the release layers are crosslinked silicone polymers.

Typical adhesive layers include film forming polymers such as polyester, polyvinylbutyral, polyvinylpyrolidone, polyurethane, polymethyl methacrylate, poly(hydroxy amino ether) and the like. Preferably, the adhesive layer is poly(hydroxy amino ether). If such layers are utilized, they preferably have a dry thickness between about 0.01 micrometer and about 5 micrometers.

Typical sub-layers include polyvinylbutyral, organosilanes, hydrolyzable silanes, epoxy resins, polyesters, polyamides, polyurethanes, silicones and the like. Preferably, the sub-layer has a dry thickness between about 20 Angstroms and about 2,000 Angstroms.

The charge transport materials, and organophotoreceptor including these compounds, are suitable for use in an imaging process with either dry or liquid toner development. Liquid toner development is generally preferred because it offers the advantages of providing higher resolution images and requiring lower energy for image fixing compared to dry toners. Examples of useful liquid toners are well-known. They typically include a colorant, a resin binder, a charge director, and a carrier liquid. A preferred resin to pigment ratio is 2:1 to 10:1, more preferably 4:1 to 8:1. Typically, the colorant, resin, and the charge director form the toner particles.

The invention will now be described further by way of the following examples.

EXAMPLES

A. Synthesis (4-n-Butoxycarbonyl-9-fluorenylidene)malononitrile

To a 1-liter 3-neck round bottom flask, equipped with thermometer, mechanical stirrer and reflux condenser were added 460 g of concentrated sulfuric acid (4.7 moles, analytical grade, commercially obtained from Sigma-Aldrich, Milwaukee, Wis.) and 100 g of diphenic acid (0.41 mole, commercially obtained from Acros Fisher Scientific Company Inc., Hanover Park, Ill.). Using heating mantle, the flask was heated to 135–145° C. for 12 minutes, and then cooled to RT. After cooled to RT, the solution was added to a 4 liter Erlenmeyer containing 3 liter of water. The mixture was stirred mechanically and was boiled gently for one hour. A yellow solid was filtered out hot, washed with hot water until the pH of the washing water was neutral, and dried in the air overnight. The yellow solid was fluorenone-4-carboxylic acid (75 g, 80% yield, m.p. 223–224° C.). A $^1$H-NMR spectrum of fluorenone-4-carboxylic acid was obtained in $d_6$-DMSO by a 300 MHz NMR from Bruker Instrument. The peaks were found at $\delta$=7.39–7.50 (m, 2H); $\delta$=7.79–7.70 (q, 2H); $\delta$=7.74–7.85 (d, 1H); $\delta$=7.88–8.00 (d, 1H); and $\delta$=8.18–8.30 (d, 1H), where d is doublet, t is triplet, m is multiplet; dd is double doublet, q is quintet.

To a 2-liter round bottom flask equipped with a mechanical stirrer and a reflux condenser with a Dean Stark apparatus were added 70 g (0.312 mole) of fluorenone-4-carboxylic acid, 480 g (6.5 mole) of n-Butanol (commercially obtained from Fisher Scientific Company Inc., Hanover Park, Ill.), 1000 ml of Toluene and 4 ml of concentrated sulfuric acid. The solution was refluxed for 5 hours with aggressive agitation and refluxing, during which ~6 g of water were collected in the Dean Stark apparatus. The flask was cooled to room temperature. The solvents were evaporated and the residue was added to 4-liter of 3% sodium bicarbonate aqueous solution with agitation. The solid was filtered off, washed with water until the pH of the water was neutral, and dried in the hood overnight. The product was n-butyl fluorenone-4-carboxylate ester (70 g, 80% yield). A $^1$H-NMR spectrum of n-butyl fluorenone-4-carboxylate ester was obtained in $CDCl_3$ by a 300 MHz NMR from Bruker Instrument. The peaks were found at $\delta$=0.87–1.09 (t, 3H); $\delta$=1.42–1.70 (m, 2H); $\delta$=1.75–1.88 (q, 2H); $\delta$=4.26–4.64 (t, 2H); $\delta$=7.29–7.45 (m, 2H); $\delta$=7.46–7.58 (m, 1H); $\delta$7.60–7.68 (dd, 1H); $\delta$=7.75–7.82 (dd, 1H); $\delta$=7.90–8.00 (dd, 1H); $\delta$=8.25–8.35 (dd, 1H).

To a 2-liter, 3-neck round bottom flask equipped with a mechanical stirrer and a reflux condenser were added 70 g (0.25 mole) of n-butyl fluorenone-4-carboxylate ester, 750 ml of absolute methanol, 37 g (0.55 mole) of malononitrile (commercially obtained from Sigma-Aldrich, Milwaukee, Wis.), 20 drops of piperidine (commercially obtained from Sigma-Aldrich, Milwaukee, Wis.). The solution was refluxed for 8 hours and the flask was cooled to room temperature. The orange crude product was filtered, washed twice with 70 ml of methanol and once with 150 ml of water, and dried in the hood for overnight. This orange crude product was recrystalized from a mixture of 600 ml of acetone and 300 ml of methanol using activated charcoal. The flask was placed at 0° C. for 16 hours. The crystals were filtered and dried in a vacuum oven at 50° C. for 6 hours to obtain 60 g of pure (4-n-butoxycarbonyl-9-fluorenylidene) malononitrile. The m.p. was 99–100° C. A $^1$H-NMR spectrum of (4-n-butoxycarbonyl-9-fluorenylidene) malononitrile was obtained in CDCl$_3$ by a 300 MHz NMR from Bruker Instrument. The peaks were found at δ=0.74–1.16 (t, 3H); δ=1.38–1.72 (m, 2H); δ=1.70–1.90 (q, 2H); δ=4.29–4.55 (t, 2H); δ=7.31–7.43 (m, 2H); δ=7.45–7.58 (m, 1H); δ=7.81–7.91 (dd, 1H); δ=8.15–8.25 (dd, 1H); δ=8.42–8.52 (dd, 1H); δ=8.56–8.66 (dd, 1H).

1,10-Bis(9-fluorenone-4-carboxyl)decane

9-Fluorenone-4-carbonyl chloride (2.44 g, 10 mmol) and 1,10-decanediol (0.87 g, 5 mmol) in the presence of triethylamine (1.01 g, 10 mmol) were refluxed overnight in THF (50 mL). THF was removed in vacuum and the compound was recrystallized using ethyl acetate to give yellow crystals; yield 64%; mp 101–102.1° C.; $^1$H-NMR in CDCl$_3$ (300 MHz) chemical shifts (ppm): 1.34–1.46 (m, 12H), 1.81 (quin, J=7.2 Hz, 4H), 4.41 (t, 8.4 Hz, 4H), 7.32–7.37 (m, 4H), 7.50 (td, J=7.8 Hz, 2H),7.70 (d, J=7.2 Hz, 2H), 7.82 (dd, J=1.2 Hz, 7.5 Hz, 2H), 7.93 (dd,, J=0.9 Hz, 7.8 Hz, 2H), 8.28 (d, J=7.8 Hz, 2H). $^{13}$C-NMR in CDCl$_3$ (75 MHz) chemical shifts (ppm): 26.14, 28.6, 29.2, 29.4, 65.8, 124.1, 126.2, 127.1, 127.3, 128.6, 129.8, 134.4, 135.1, 135.6, 136.0, 143.2, 144.0, 166.8, 193.0.

1,8-Bis(9-fluorenone-4-carboxyl)octane 1,8-Bis(9-fluorenone-4-carboxyl)octane may be prepared according to the following procedure. 9-Fluorenone-4-carbonyl chloride (2.44 g, 10 mmol) and 1,8-octanediol (0.73 g, 5 mmol) in the presence of triethylamine (1.01 g, 10 mmol) are refluxed overnight in THF (50 mL). THF is removed in vacuum and the compound is recrystallized using ethyl acetate to give yellow crystals.

Compound (2)

A mixture of 4-Methylsulphonylphenylhydrazine hydrochloride (3.5 g, 11.2 mmol), 1,10-bis(9-Fluorenone-4-carboxyl)decane (3.28 g, 5.6 mmol) and sodium acetate (0.92 g, 11.2 mmol) in ethanol (50 mL) was refluxed for 5 h. The resulting mixture was cooled to 20° C. The precipitate was filtered. The solid was suspended in 100 mL of water and filtered. The filtered cake was washed with ethanol and water to give pure Compound (2) as yellow prisms; yield 45%; m.p. 178–179° C.; $^1$H-NMR in CDCl3 (300 MHz) chemical shifts (ppm): 1.33–1.43 (m, 12H), 1.77–1.80 (m, 4H), 3.06 (s, 3H), 3.07(s, 3H), 4.32–4.38 (m, 2H), 4.40-4.47 (m, 2H), 7.26–7.42 (m, 10H), 7.62–8.05 (m, 10H), 9.04–9.18 (m, 2H)

Compound (3)

Compound (3) can be prepared by the following procedure. A mixture of 4-Methylsulphonylphenylhydrazine hydrochloride (3.5 g, 11.2 mmol), 1,8-Bis(9-fluorenone-4-carboxyl)octane (3.12 g, 5.6 mmol) and sodium acetate (0.92 g, 11.2 mmol) in ethanol (50 mL) was refluxed for 5 h. The resulting mixture was cooled to 20° C. The precipitate was filtered. The solid was suspended in 100 mL of water and filtered. The filtered cake was washed with ethanol and water to give pure Compound (3) as yellow prisms.

N-(5-Benzotriazolyl)-N-phenylhydrazine

N-(5-benzotriazolyl)-N-phenylhydrazine can be prepared according to the procedure described below. To a mixture of phenylhydrazine (97 g, 0.9 mole, commercially available from Aldrich, Milwaukee, Wis.) and 5-chlorobenzotriazole (15.4 g, 0.1 mole, commercially available from Aldrich, Milwaukee, Wis.) heated to boiling temperature, sodium is slowly added until there is no more discharge of red coloration. After boiling for some time the mixture is cooled to room temperature. The product is isolated and purified.

Compound (4)

Compound (4) can be prepared by the following procedure. 1,10-Bis(9-fluorenone-4-carboxyl)decane (37.5 g, 64 mmol) and N-(5-benzotriazolyl)-N-phenylhydrazine (29.25 g, 130 mmol, 2 equiv.) are combined in tetrahydrofuran (600 mL) and heated at reflux with stirring for 2 hours. Compound (4) is isolated and purified.

Compound (5)

Compound (5) can be prepared by the following procedure. 1,8-Bis(9-fluorenone-4-carboxyl)octane (35.71 g, 64 mmol) and N-(5-benzotriazolyl)-N-phenylhydrazine (29.25 g, 130 mmol, 2 equiv.) are combined in tetrahydrofuran (600 mL) and heated at reflux with stirring for 2 hours. Compound (5) is isolated and purified.

N-Phenyl-N-sulfolan-3-ylhydrazine

N-Phenyl-N-sulfolan-3-ylhydrazine can be prepared according to the procedure described in Great Britain Patent No. 1,047,525 by Mason, which is incorporated herein by reference. To a mixture of 0.5 mole of butadiene sulfone (commercially available from Aldrich, Milwaukee, Wis.) and 0.55 mole of phenylhydrazine (commercially available from Aldrich, Milwaukee, Wis.) was added 0.005 mole 40% aqueous potassium hydroxide solution. The mixture was kept for 2 hours at 60° C. whereupon a solid separated. After 10 hours the solid was filtered off to give N-phenyl-N-sulfolan-3-ylhydrazine (53%) having a melting point of 120–121° C. (MeOH).

Compound (6)

A mixture of 1,10-bis(9-fluorenone-4-carboxyl)decane (5.86 g, 10 mmol) and N-phenyl-N-sulfolan-3-ylhydra (4.6 g, 20 mmol) was refluxed in ethanol for 5 hours. The mixture was cooled to 0° C. The compound was filtered and orange fine crystals of pure Compound (6) were obtained; yield 42%; m.p. 115.9–116.1° C.; $^1$H-NMR in CDCl3 (300 MHz) chemical shifts (ppm): 1.19–1.42 (m, 12H), 1.76–1.81 (m, 4H), 2.57–2.71 (m, 4H), 3.08–3.17(m, 2H), 3.24–3.33 (m, 2H), 3.48–3.59 (m, 2H), 3.74–3.85 (m, 2H), 4.38–4.42 (m, 4H), 4.77 (t, J=7.0 Hz, 2H), 6.94–7.07 (m, 8H), 7.2–7.35 (m, 8H), 7.37–7.42 (m, 2H), 7.50 (d, J=7.8 Hz, 1H), 7.70 (dd, J=7.8 Hz, 16.8 Hz, 1H), 7.84 (d, J=7.5 Hz, 1H), 8.03–8.12 (m, 1H), 8.22 (t, 7.8 Hz, 2H).

Compound (7)

A mixture of 1,8-Bis(9-fluorenone-4-carboxyl)octane (5.58 g, 10 mmol) and N-phenyl-N-sulfolan-3-ylhydrazine (4.6 g, 20 mmol) was refluxed in ethanol for 5 hours. The mixture was cooled 0° C. The compound was filtered and orange fine crystals of pure Compound (7) were obtained.

5-Methyl-1-Phenyl-3-(1-phenylhydrazino)pyrazole

5-Methyl-1-phenyl-3-(1-phenylhydrazino)pyrazole can be prepared according to the procedure described in J. Chem. Soc. C (1971), (12), 2314–17 by Boyd et el., which is incorporated herein by reference.

Compound (8)

Compound (8) can be prepared by the following procedure. 1,10-Bis(9-fluorenone-4-carboxyl)decane (37.5 g, 64 mmol) and 5-methyl-1-phenyl-3-(1-phenylhydrazino) pyrazole (34.32 g, 130 mmol, 2 equiv.) are combined in tetrahydrofuran (600 mL) and heated at reflux with stirring for 2 hours. Compound (8) is isolated and purified.

Compound (9)

Compound (9) can be prepared by the following procedure. 1,8-Bis(9-fluorenone-4-carboxyl)octane (35.71 g, 64 mmol) and 5-methyl-1-phenyl-3-(1-phenylhydrazino) pyrazole (34.32 g, 130 mmol, 2 equiv.) are combined in tetrahydrofuran (600 mL) and heated at reflux with stirring for 2 hours. Compound (9) is isolated and purified.

N-(4-Stilbenyl)-N-phenylhydrazine

N-(4-Stilbenyl)-N-phenylhydrazine can be prepared according to the procedure described in Zh. Org. Khim. (1967), 3(9), 1605-3 by Matevosyan et el., which is incorporated herein by reference. To a mixture of phenylhydrazine (97 g, 0.9 mole, commercially available from Aldrich, Milwaukee, Wis.) and p-chlorostilbene (21.4 g, 0.1 mole, commercially available from Spectrum Quality Products, Inc., Gardena, Calif; Web: www.spectrumchemical.com) heated to boiling temperature, sodium was slowly added until there was no more discharge of red coloration. After boiling for some time the mixture was dissolved in 1750 ml of ethanol and cooled to −15° C. The precipitated product was recrystallized to give 28% of N-(4-stilbenyl)-N-phenylhydrazine.

Compound (10)

Compound (10) can be prepared by the following procedure. 1,10-Bis(9-fluorenone-4-carboxyl)decane (37.5 g, 64 mmol) and N-(4-stilbenyl)-N-phenylhydrazine (37.18 g, 130 mmol, 2 equiv.) are combined in tetrahydrofuran (600 mL) and heated at reflux with stirring for 2 hours. Compound (10) is isolated and purified.

Compound (11)

Compound (11) can be prepared by the following procedure. 1,8-Bis(9-fluorenone-4-carboxyl)octane (35.71 g, 64 mmol) and N-(4-stilbenyl)-N-phenylhydrazine (37.18 g, 130 mmol, 2 equiv.) are combined in tetrahydrofuran (600 mL) and heated at reflux with stirring for 2 hours. Compound (11) is isolated and purified.

1-Phenyl-1-(1-benzyl-1H-tetrazol-5-yl)hydrazine

1-Phenyl-1-(1-benzyl-1H-tetrazol-5-yl)hydrazine can be prepared according to the procedure described in Tetrahedron (1983), 39(15), 2599–608 by Atherton et el., which is incorporated herein by reference.

Compound (12)

Compound (12) can be prepared by the following procedure. 1,10-Bis(9-fluorenone-4-carboxyl)decane (37.5 g, 64 mmol) and 1-phenyl-1-(1-benzyl-1H-tetrazol-5-yl)hydrazine (34.58 g, 130 mmol, 2 equiv.) are combined in tetrahydrofuran (600 mL) and heated at reflux with stirring for 2 hours. Compound (12) is isolated and purified.

Compound (13)

Compound (13) can be prepared by the following procedure. 1,8-Bis(9-fluorenone-4-carboxyl)octane (35.71 g, 64 mmol) and 1-phenyl-1-(1-benzyl-1H-tetrazol-5-yl)hydrazine (34.58 g, 130 mmol, 2 equiv.) are combined in tetrahydrofuran (600 mL) and heated at reflux with stirring for 2 hours. Compound (13) is isolated and purified.

1,1-Dinaphthylhydrazine 1,1-Dinaphthylhydrazine can be prepared according to the procedure described in Staschkow, L. I.; Matevosyan, R. O. Journal of the General Chemistry (1964) 34, 136, which is incorporated herein by reference. A suspension of 0.07 mole of the naphthyl nitrosamine in 750 ml of ether is cooled to 5–8° C. and treated with 150 g of zinc dust. Acetic acid (70 ml) is then added drop wise with stirring. To complete the reaction, 40 g of zinc dust is added. The reaction mixture is heated and filtered from the sludge. The mother liquor is washed with 10% sodium carbonate solution and dried with solid KOH. The ether is distilled off to give the crystalline hydrazine, which is crystallized from ethanol or butanol.

Compound (14)

Compound (14) can be prepared by the following procedure. 1,10-Bis(9-fluorenone-4-carboxyl)decane (37.5 g, 64 mmol) and dinaphthylhydrazine (37.18 g, 130 mmol, 2 equiv.) are combined in tetrahydrofuran (600 mL) and heated at reflux with stirring for 2 hours. Compound (14) is isolated and purified.

Compound (15)

Compound (15) can be prepared by the following procedure. 1,8-Bis(9-fluorenone-4-carboxyl)octane (35.71 g, 64 mmol) and dinaphthylhydrazine (37.18 g, 130 mmol, 2 equiv.) are combined in tetrahydrofuran (600 mL) and heated at reflux with stirring for 2 hours. Compound (15) is isolated and purified.

N-4-[(9H-Fluoren-9-ylidene)benzyl]-N-phenylhydrazine

N-4-[(9H-fluoren-9-ylidene)benzyl]-N-phenylhydrazine can be prepared according to the procedure similar to that described in Zh. Org. Khim. (1967), 3(9), 1605-3 by Matevosyan et el., which is incorporated herein by reference. To a mixture of phenylhydrazine (97 g, 0.9 mole, commercially available from Aldrich, Milwaukee, Wis.) and p-9-(4-chlorobenzylidene)fluorene (28.9 g, 0.1 mole, commercially available from from Aldrich, Milwaukee, Wis.) heated to boiling temperature, sodium was slowly added until there was no more discharge of red coloration. After boiling for some time the mixture was dissolved in 1750 ml of ethanol and cooled to −15° C. The precipitated product was recrystallized to give N-4-[(9H-fluoren-9-ylidene)benzyl]-N-phenylhydrazine.

Compound (16)

Compound (16) can be prepared by the following procedure. 1,10-Bis(9-fluorenone-4-carboxyl)decane (37.5 g, 64 mmol) and N-4-[(9H-fluoren-9-ylidene)benzyl]-N-phenylhydrazine (46.8 g, 130 mmol, 2 equiv.) are combined in tetrahydrofuran (600 mL) and heated at reflux with stirring for 2 hours. Compound (16) is isolated and purified.

Compound (17)

Compound (17) can be prepared by the following procedure. 1,8-Bis(9-fluorenone-4-carboxyl)octane (35.71 g, 64 mmol) and N-4-[(9H-fluoren-9-ylidene)benzyl]-N-phenylhydrazine (46.8 g, 130 mmol, 2 equiv.) are combined in tetrahydrofuran (600 mL) and heated at reflux with stirring for 2 hours. Compound (17) is isolated and purified.

N-Pyrrol-2-yl-N-phenylhydrazine

N-Pyrrol-2-yl-N-phenylhydrazine can be prepared according to the procedure described in Japanese Patent No. 05148210 by Myamoto, which is incorporated herein by reference.

Compound (18)

Compound (18) can be prepared by the following procedure. 1,10-Bis(9-fluorenone-4-carboxyl)decane (37.5 g, 64 mmol) and N-pyrrol-2-yl-N-phenylhydrazine (22.49 g, 130 mmol, 2 equiv.) are combined in tetrahydrofuran (600 mL) and heated at reflux with stirring for 2 hours. Compound (18) is isolated and purified.

Compound (19)

Compound (19) can be prepared by the following procedure. 1,8-Bis(9-fluorenone-4-carboxyl)octane (35.71 g, 64 mmol) and N-pyrrol-2-yl-N-phenylhydrazine (22.49 g, 130 mmol, 2 equiv.) are combined in tetrahydrofuran (600 mL) and heated at reflux with stirring for 2 hours. Compound (19) is isolated and purified.

Example 1

Example 1 was a single layer organophotoreceptor that was ring coated onto a 30 mm×250 mm, anodized aluminum drum core at a setting to produce a nominal thickness of 13 microns. The coating solution for the single layer organophotoreceptor was prepared by combining 1.87 g of MPCT-10 (a charge transfer material, commercially obtained from Mitsubishi Paper Mills, Tokyo, Japan), 0.54 g of Compound 2, and 9.37 g of tetrahydrofuran and shaken until the components dissolved. Added to this mixture was 7.4 g of a 14 wt % polyvinyl butyral resin (BX-1, commercially obtained from Sekisui Chemical Co. Ltd., Japan) in tetrahydrofuran pre-mix solution and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. Tinuvin 292 (0.018 g T-292 in 5.68 g tetrahydrofuran) light stabilizer was added to the coating solution.

The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of MEK on a horizontal sand mill (model LMC12 DCMS, commercially obtained from Netzsch Incorporated, Exton, Pa.) with 1-micron zirconium beads using recycle mode for 4 hours.

After mixing the solution on a mechanical shaker for~1 hour, the single layer coating solution was coated onto drum core substrate described above and dried in a convection oven at 100° C. for 15–30 minutes.

Example 2

Example 2 single layer organophotoreceptor coating solution was prepared by combining 1.87 g of MPCT-10 (a charge transfer material, commercially obtained from Mitsubishi Paper Mills, Tokyo, Japan), 0.54 g of Compound 6 and 9.37 g of tetrahydrofuran and shaken until the components dissolved. Added to this mixture was 7.4 g of a 14 wt % polyvinyl butyral resin (BX-1, commercially obtained from Sekisui Chemical Co. Ltd., Japan) in tetrahydrofuran pre-mix solution and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. Tinuvin® 292 (0.018 g T-292 in 5.68 g tetrahydrofuran) light stabilizer was added to the coating solution.

The CGM mill-base was prepared as described in Example 1.

After mixing the solution on a mechanical shaker for ~1 hour, the single layer coating solution was coated onto the drum substrate described in Example 1 using a ring coater and dried in a convection oven at 100° C. for 15–30 minutes.

Comparative Example A

Comparative Example A single layer organophotoreceptor coating solution was prepared by combining 1.87 g of MPCT-10 (a charge transfer material, commercially obtained from Mitsubishi Paper Mills, Tokyo, Japan), 0.54 g of a (4-n-butoxycarbonyl-9-fluorenylidene)malononitrile, and 9.37 g of tetrahydrofuran and shaken until the components dissolved. Added to this mixture was 7.4 g of a 14 wt % polyvinyl butyral resin (BX-1, commercially obtained from Sekisui Chemical Co. Ltd., Japan) in tetrahydrofuran pre-mix solution and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. Tinuvin® 292 (0.018 g T-292 in 5.68 g tetrahydrofuran) light stabilizer was added to the coating solution.

The CGM mill-base was prepared as described in Example 1. After mixing the solution on a mechanical shaker for ~1 hour, the single layer coating solution was coated onto the substrate described in Example 1 using a ring coater and dried in a convection oven at 100° C. for 15–30 minutes.

Electrostatic Testing

Electrostatic cycling performance of the charge transfer compounds of this invention is determined using in-house designed and developed test bed that is capable of testing the ring coated 30 mm drums. Electrostatic evaluation on the 30 mm drum test bed is designed to accelerate electrostatic fatigue during extended cycling by increasing the charge-discharge cycling frequency and decreasing the recovery time as compared to larger diameter drum formats. In this electrostatic cycling tester, the drum rotated at a rate of 12.7 cm/sec (5 ips) and the location of each station in the tester (distance and elapsed time per cycle) is given as:

Electrostatic test stations around the 30 mm drum at 12.7 cm/sec.

| Station | Degrees | Total Distance, cm | Total Time, sec |
| --- | --- | --- | --- |
| Erase Bar Center | 0° | Initial, 0 cm | Initial, 0 s |
| Scorotron Charger | 87.3° | 2.28 | 0.18 |
| Laser Strike | 147.7° | 3.86 | 0.304 |
| Probe #1 | 173.2° | 4.53 | 0.357 |
| Probe #2 | 245.9° | 6.43 | 0.506 |
| Erase Bar Center | 360° | 9.42 | 0.742 |

From the above table, the first electrostatic probe (TREK™ 344 electrostatic meter) is located 0.34 s after the laser strike station and 0.78 s after the scorotron. Also, the second probe (TREK™ 344 electrostatic meter) is located 1.21 s from the first probe and 1.99 s from the scorotron. All measurements were performed at ambient temperature and relative humidity.

Electrostatic measurements were obtained as a compilation of several tests. The first three diagnostic tests (prodstart, VlogE initial, dark decay initial) are designed to evaluate the electrostatic cycling of a new, fresh sample and the last three, identical diagnostic test (prodend, V log E final, dark decay final) are run after cycling of the sample (longrun). The laser is operated at 780 nm, 600 dpi, 50 um spot size, 60 nanoseconds/pixel expose time, 1,800 lines per second scan speed, and a 100% duty cycle. The duty cycle is the percent exposure of the pixel clock period, i.e., the laser is on for the full 60 nanoseconds per pixel at a 100% duty cycle.

Electrostatic Test Suite:

1) PRODTEST: The erase bar was turned on during this diagnostic test and the sample recharged at the beginning of each cycle (except where indicated as charger off). The test sequence was as follows. The sample was completely charged for three complete drum revolutions (laser off); discharged with the laser (780 nm, 600 dpi, 50 um spot size, expose 60 nanoseconds/pixel, run at a scan speed of 1,800 lines per second, and use a 100% duty cycle) on the forth cycle; completely charged for the next three cycles (laser off); discharged with only the erase lamp @ 720 nm on the eighth cycle (corona and laser off); and, finally, completely charged for the last three cycles (laser off).

2) V LOG E: This test measures the photoinduced discharge of the photoconductor to various laser intensity levels by monitoring the discharge voltage of the belt as a function of the laser power (exposure duration of 50 ns). The complete sample was charged and discharged at incremental laser power levels per each drum revolution. A semi-logarithmic plot was generated (voltage verses log E) to identify the sample's sensitivity and operational power settings. The functional photosensitivity (Sens.) was determined from this diagnostic test.

3) DARK DECAY: This test measures the loss of charge acceptance in the dark with time without laser or erase illumination and can be used as an indicator of i) the injection of residual holes from the charge generation layer to the charge transport layer, ii) the thermal liberation of trapped charges, and iii) the injection of charge from the surface or aluminum ground plane. After the belt has been completely charged, it was stopped and the probes measured the surface voltage over a period of 90 seconds. The decay in the initial voltage was plotted verses time.

4) LONGRUN: The belt was electrostatically cycled for 100 to 4,000 drum revolutions according to the following sequence per each belt-drum revolution. The belt was charged by the corona, the laser was cycled on and off (80–100° sections) to discharge a portion of the belt and, finally, the erase lamp discharged the whole belt in preparation for the next cycle. The laser was cycled so that the first section of the belt was never exposed, the second section was always exposed, the third section was never exposed, and the final section was always exposed. This pattern was repeated for a total of 100 to 4,000 drum revolutions and the data was recorded periodically, after every "total drum revolutions" /twenty cycles.

5) After the last cycle (long run test), the PRODTEST, V LOG E, DARK DECAY diagnostic tests were run again.

The following Table shows the results from the prodstart and prodend diagnostic tests. The values for the charge acceptance voltage (Vacc, probe #1 average voltage obtained from the third cycle), discharge voltage (Vdis, probe #1 average voltage obtained from the fourth cycle), functional dark decay voltage (Vdd, average voltage difference between probes 1 & 2 obtained from the third cycle), and the residual voltage (Vres, probe 1, average voltage obtained from the eighth cycle) are reported for the initial and final cycles.

TABLE 1

The Electrostatic Test Results after 500 Cycles.

| Sample | Prodstart | | | | | Prodstop | | | | |
| --- | --- | --- | --- | --- | --- | --- | --- | --- | --- | --- |
| | Vacc | Vdis | Sens. | Vdd | Vres | Vacc | Vdis | Sens. | Vdd | Vres |
| Comparative Example A | 601 | 40 | 419 | 51 | 51 | 586 | 39 | 397 | 39 | 9 |
| Example 1 | 863 | 150 | 236 | 20 | 61 | 625 | 145 | 236 | 23 | 70 |
| Example 2 | 740 | 128 | 222 | 28 | 59 | 523 | 103 | 222 | 29 | 58 |

In the above table, the radiation sensitivity (Sensitivity at 780 nm in m2/J) of the xerographic process was determined from the information obtained during the VLOGE diagnostic run by calculating the reciprocal of the product of the laser power required to discharge the photoreceptor to ½ of its initial potential, the exposure duration, and 1/spot size.

What is claimed is:

1. An organophotoreceptor comprising:
   (a) at least one charge transport material comprising a fluorenone hydrazones having a combination of groups thereon, the combination of groups being selected from the group consisting of a) at least two fluorenone alkylsulfonylphenylhydrazone groups, b) at least two fluorenone pyrrolylhydrazone groups, c) at least two fluorenone benzotriazolylhydrazone groups, d) at least two fluorenone sulfolanylhydrazone groups, e) at least two fluorenone pyrazolylhydrazone groups, f) at least two fluorenone naphthylhydrazone groups, g) at least two fluorenone tetrazolylhydrazone groups, h) at least two fluorenone stilbenylhydrazone groups, and i) at least two fluorenone (9H-fluoren-9-ylidene) benzylhydrazone groups;
   (b) a charge generating compound; and
   (c) an electrically conductive substrate.

2. An organophotoreceptor comprising:
   (a) a charge transport material having a formula selected from the group consisting of:

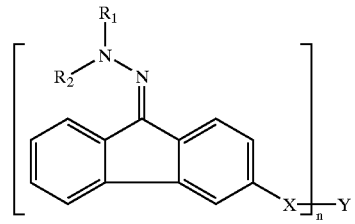

A) where n is an integer between 2 and 6, inclusive;

$R_1$ is hydrogen, an alkyl group, or an aryl group;

$R_2$ is an alkylsulfonylphenyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

B) where n is an integer between 2 and 6, inclusive;

$R_1$ is hydrogen, an alkyl group, or an aryl group;

$R_2$ is pyrrolyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

C) where n is an integer between 2 and 6, inclusive;

$R_1$ is hydrogen, an alkyl group, or an aryl group;

$R_2$ is benzotriazolyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

D) where n is an integer between 2 and 6, inclusive;

$R_1$ is hydrogen, an alkyl group, or an aryl group;

$R_2$ is sulfolanyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

E) where n is an integer between 2 and 6, inclusive;

$R_1$ is hydrogen, an alkyl group, or an aryl group;

$R_2$ is a pyrazolyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

F) where n is an integer between 2 and 6, inclusive;

$R_1$ is hydrogen, an alkyl group, or an aryl group;

$R_2$ is tetrazolyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

G) where n is an integer between 2 and 6, inclusive;

$R_1$ is hydrogen, an alkyl group, or an aryl group;

$R_2$ is stilbenyl or one of its derivatives;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group;

H) where n is an integer between 2 and 6, inclusive;

$R_1$ is hydrogen, an alkyl group, or an aryl group;

$R_2$ is (9H-fluoren-9-ylidene)benzyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group; and I) where n is an integer between 2 and 6, inclusive;

$R_1$ is hydrogen, an alkyl group, or an aryl group;

$R_2$ is naphthyl group;

X is a linking group having the formula —$(CH_2)_m$—, branched or linear, where m is an integer between 0 and 20, inclusive, and one or more of the methylene groups is optionally replaced by oxygen atom, a carbonyl group, urethane, urea, an ester group, a —$NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear —$(CH_2)_p$— group where p is an integer between 0 and 10, an aryl group, a cycloalkyl group, a cyclosiloxyl group, a heterocyclic group, or a CR$_7$ group where R$_7$ is hydrogen atom, an alkyl group, or an aryl group;

(b) a charge generating compound; and (c) an electrically conductive substrate.

3. The organophotoreceptor of claim 1 wherein the at least one charge transport material comprises a compound of the formula:

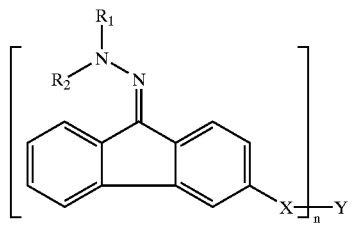

where n is an integer between 2 and 6, inclusive;

R$_1$ is hydrogen, an alkyl group, or an aryl group;

R$_2$ is an alkylsulfonylphenyl group, pyrrolyl group, benzotriazolyl group, sulfolanyl group, pyrazolyl group, tetrazolyl group, stilbenyl group, (9H-fluoren-9-ylidene)benzyl group, naphthyl group, or one of their derivatives;

X is a linking group having the formula —(CH$_2$)$_m$—, branched or linear, where m is an integer between 0 and 20, inclusive, and one or more of the methylene groups is optionally replaced by oxygen atom, a carbonyl group, urethane, urea, an ester group, a —NR$_3$ group, a CHR$_4$ group, or a CR$_5$R$_6$ group where R$_3$, R$_4$, R$_5$, and R$_6$ are, independently, H, an alkyl group, or an aryl group; and Y is a bond, carbon atom, nitrogen atom, oxygen atom, sulfur atom, a branched or linear —(CH$_2$)$_p$— group where p is an integer between 0 and 10, an aryl group, a cycloalkyl group, a cyclosiloxyl group, a heterocyclic group, or a CR$_7$ group where R$_7$ is hydrogen atom, an alkyl group, or an aryl group.

4. An organophotoreceptor according to claim 2 wherein said organophotoreceptor further comprises a second charge transport material.

5. An organophotoreceptor according to claim 2 comprising:

(a) a charge transport layer comprising said charge transport material and a polymeric binder;

(b) a charge generating layer comprising said charge generating compound and a polymeric binder; and (c) said electrically conductive substrate.

6. The organophotoreceptor of claim 2 wherein the charge transport material has the formula

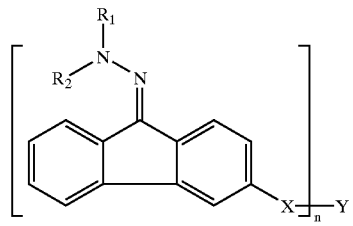

where n is an integer between 2 and 6, inclusive;

R$_1$ is hydrogen, an alkyl group, or an aryl group;

R$_2$ is an alkylsulfonylphenyl group, pyrrolyl group, benzotriazolyl group, sulfolanyl group, pyrazolyl group, tetrazolyl group, stilbenyl group, (9H-fluoren-9-ylidene)benzyl group, naphthyl group, or one of their derivatives;

X is a linking group having the formula —(CH$_2$)$_m$—, branched or linear, where m is an integer between 0 and 20, inclusive, and one or more of the methylene groups is optionally replaced by oxygen atom, a carbonyl group, urethane, urea, an ester group, a —NR$_3$ group, a CHR$_4$ group, or a CR$_5$R$_6$ group where R$_3$, R$_4$, R$_5$, and R$_6$ are, independently, H, an alkyl group, or an aryl group; and Y is a bond, carbon atom, nitrogen atom, oxygen atom, sulfur atom, a branched or linear —(CH$_2$)$_p$— group where p is an integer between 0 and 10, an aryl group, a cycloalkyl group, a cyclosiloxyl group, a heterocyclic group, or a CR$_7$ group where R$_7$ is hydrogen atom, an alkyl group, or an aryl group.

7. The organophotoreceptor of claim 2 wherein the charge transport material has the formula

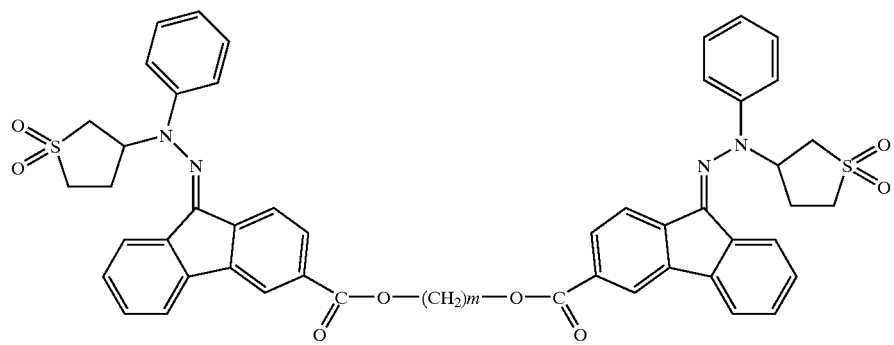

where m is an integer between 2 and 20.

8. The organophotoreceptor of claim 2 wherein the charge transport material has the formula

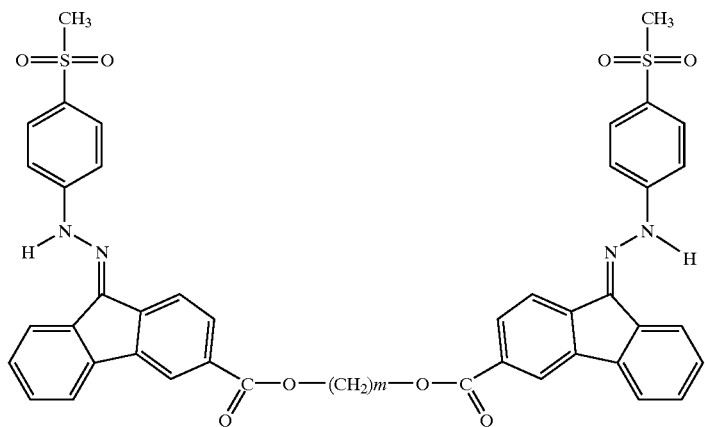

where m is integer between 2 and 20.

9. The organophotoreceptor of claim 2 wherein the charge transport material has the formula

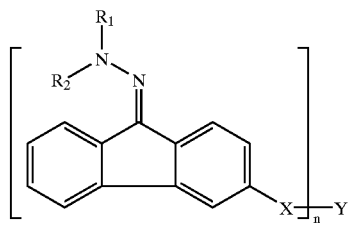

where n is an integer between 2 and 6, inclusive;

$R_1$ and $R_2$ are, independently, naphthyl or one of its derivatives;

X is a linking group having the formula $-(CH_2)_m-$, branched or linear, where m is an integer between 0 and 20, inclusive, and one or more of the methylene groups is optionally replaced by oxygen atom, a carbonyl group, urethane, urea, an ester group, a $-NR_3$ group, a $CHR_4$ group, or a $CR_5R_6$ group where $R_3$, $R_4$, $R_5$, and $R_6$ are, independently, H, an alkyl group, or an aryl group; and Y is a bond, carbon atom, nitrogen atom, oxygen atom, sulfur atom, a branched or linear $-(CH_2)_p-$ group where p is an integer between 0 and 10, an aryl group, a cycloalkyl group, a cyclosiloxyl group, a heterocyclic group, or a $CR_7$ group where $R_7$ is hydrogen atom, an alkyl group, or an aryl group.

10. The organophotoreceptor of claim 1 wherein the charge transport material is represented by one of the formulae selected from the group consisting of:

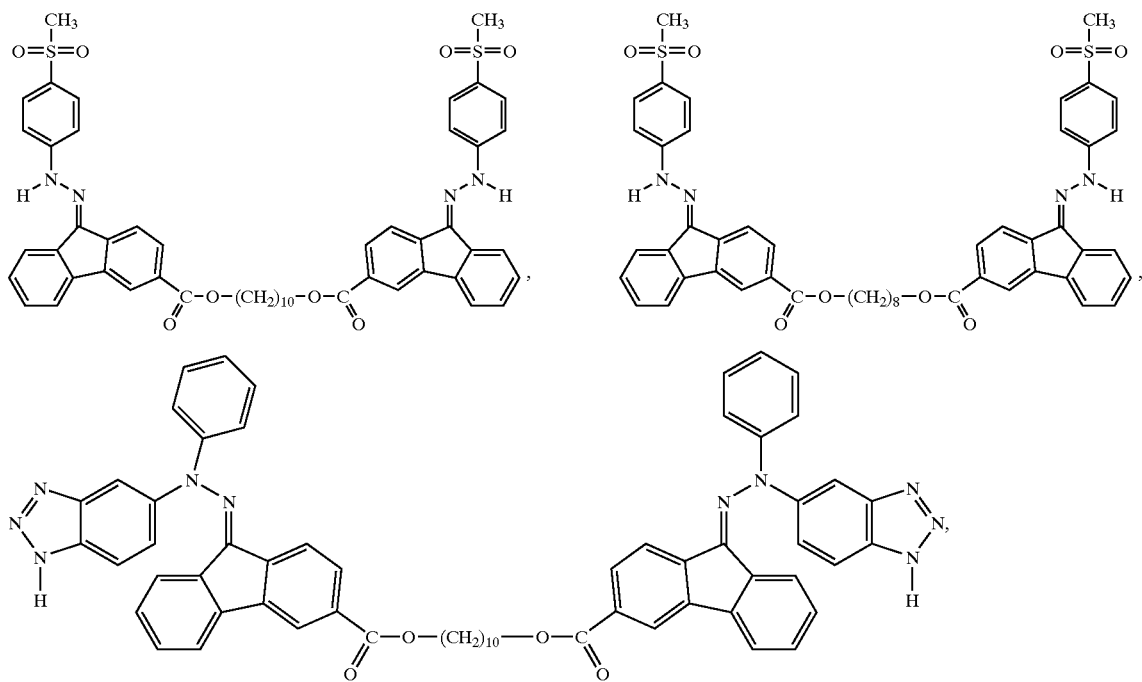

-continued
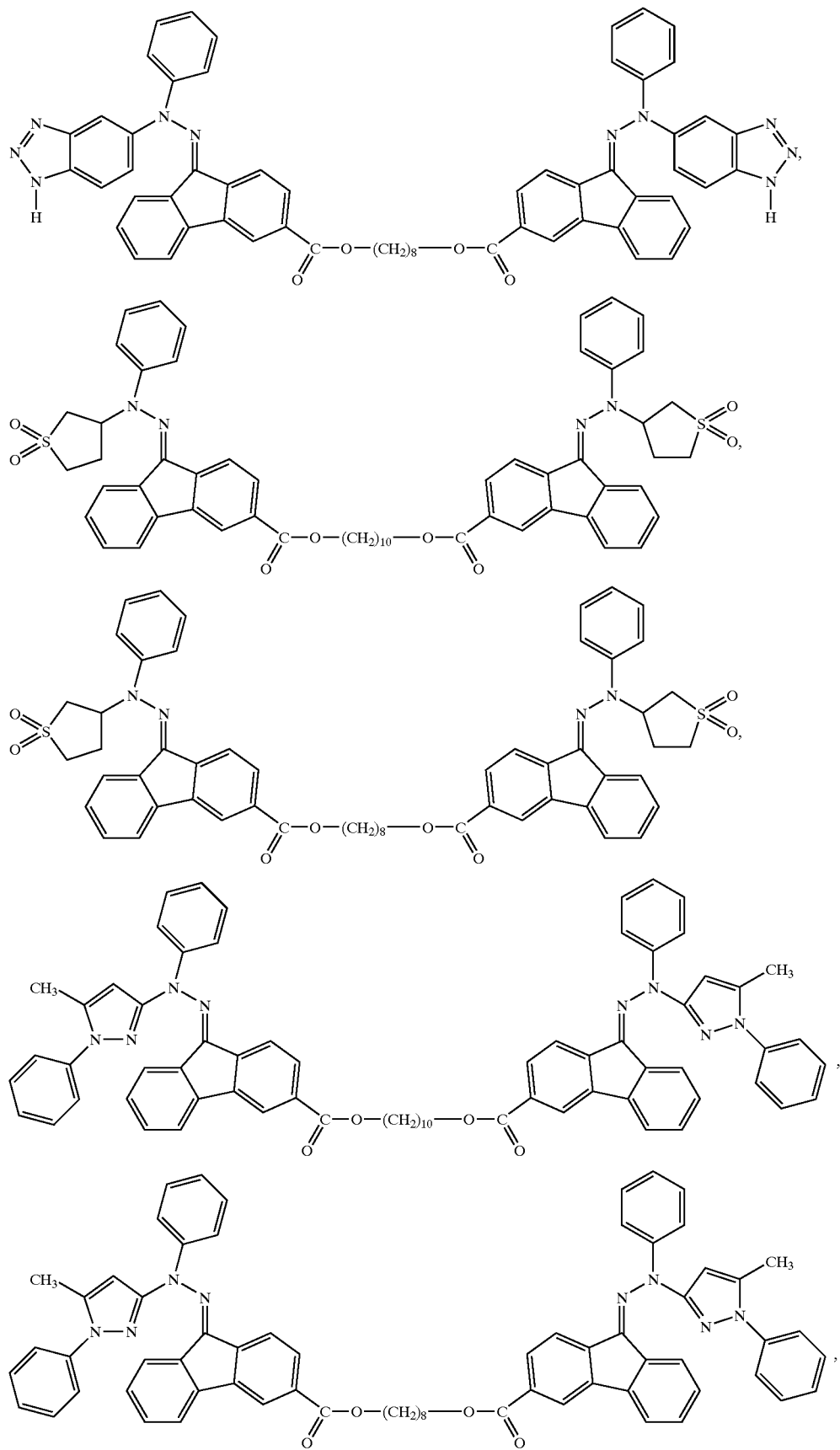

-continued
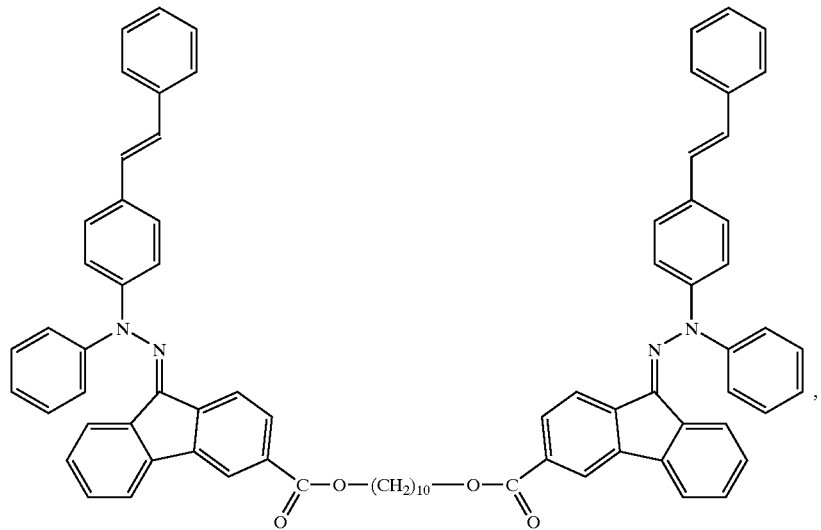
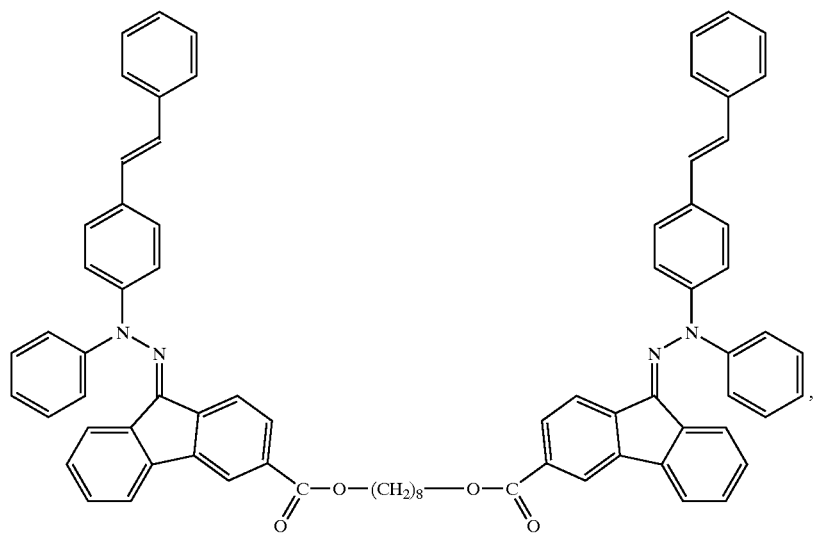
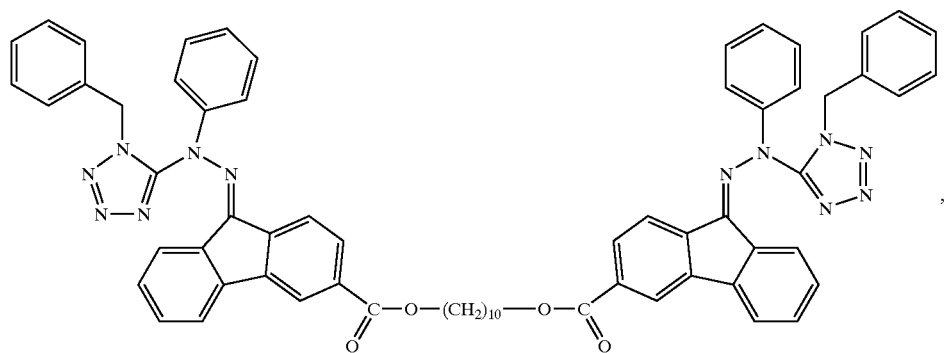

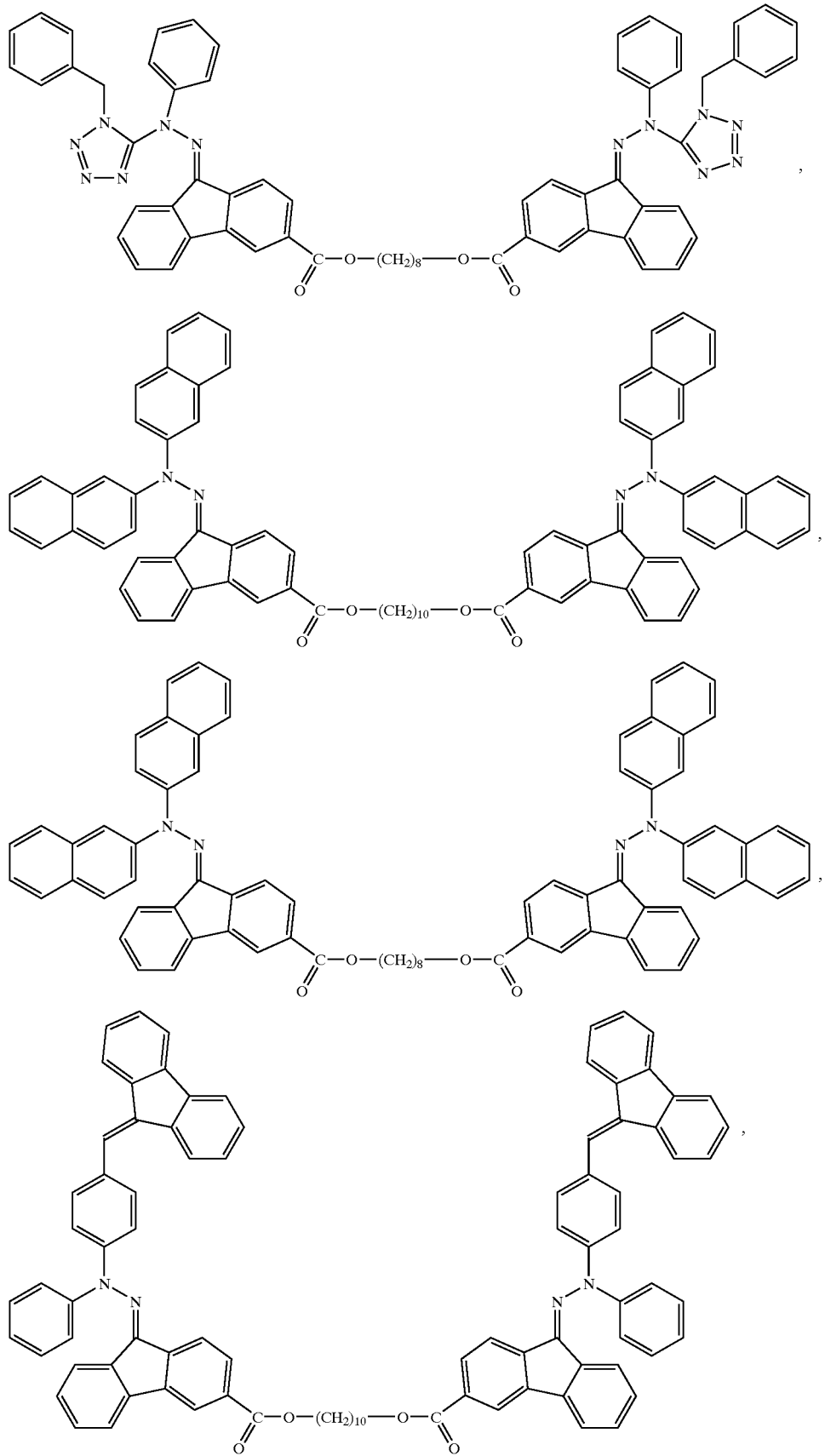

-continued
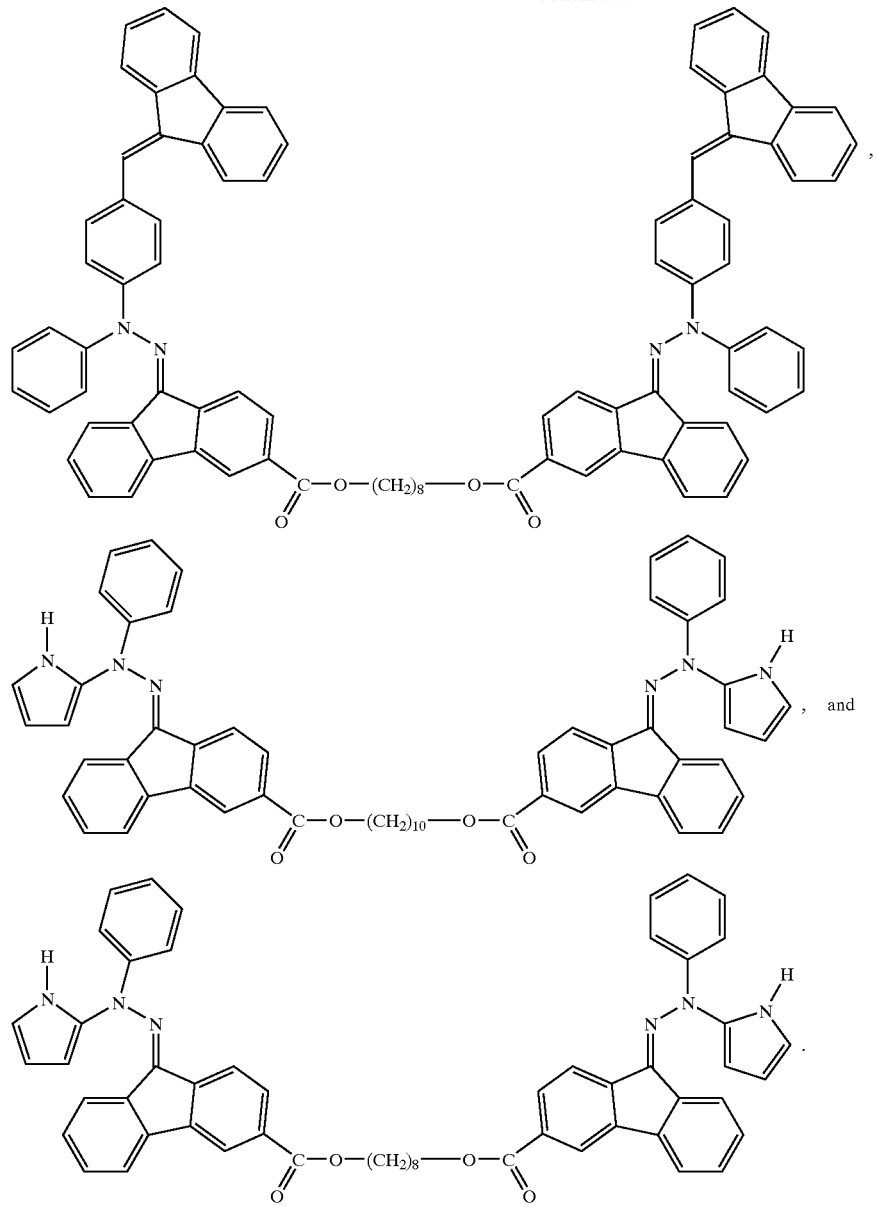
* * * * *